(12) United States Patent
Freire (10) Patent No.: US 6,823,267 B2
(45) Date of Patent: Nov. 23, 2004

(54) STRUCTURAL PREDICTION OF ALLOSTERISM

(75) Inventor: Ernesto Freire, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 233 days.

(21) Appl. No.: 09/950,047

(22) Filed: Sep. 12, 2001

(65) Prior Publication Data

US 2003/0009291 A1 Jan. 9, 2003

Related U.S. Application Data

(60) Provisional application No. 60/232,060, filed on Sep. 12, 2000.

(51) Int. Cl.[7] .............................. G01N 33/48; G06G 7/60

(52) U.S. Cl. ............................................. 702/27; 703/11

(58) Field of Search .............................. 702/27; 703/11

(56) References Cited

PUBLICATIONS

Freire The propagation of binding interactions to remote sites in proteins:Analysis of the binding of the monoclonal antibody D1.3 to lysozyme. Proc. Natl. Acad. Sci. USA vol. 96 pp. 10118–10122 (1999).*

* cited by examiner

*Primary Examiner*—John S. Brusca
(74) *Attorney, Agent, or Firm*—Witham, Curtis & Christofferson, P.C.

(57) ABSTRACT

The present invention provides a computer-assisted method for creating and displaying a model of a molecule in which residues that are affected by the binding of a ligand to the molecule are highlighted, making it possible to trace the path of propagation of a binding signal through the molecule. In order to carry out the method, the binding site determinants of the molecule are determined and the binding constant for the ligand is calculated. The states of a conformational ensemble that are binding competent are identified, and the Gibbs energy and probability of each state and the stability constant per residue of the molecule are calculated in the presence and absence of the ligand. Those residues that display a difference in stability constant in the presence vs absence of ligand are those which are affected by the binding of the ligand.

4 Claims, 3 Drawing Sheets

STRUCTURAL PREDICTION OF ALLOSTERISM

This application claims priority to U.S. Provisional Patent Application Ser. No. 60/232,060 filed Sep. 12, 2000.

This invention was made using funds from grants from the National Institutes of Health having grant No. GM51362. The government may have certain rights in this invention.

BACKGROUND OF THE INVENTION

1. Field of the Invention

The invention generally relates to the analysis of ligand binding to a macromolecule. In particular, the invention provides a method for tracing the path of a ligand binding signal through the three-dimensional structure of a macromolecule by determining the stability of the residues of the macromolecule in the presence and absence of the ligand.

2. Background of the Invention

The process of developing new drugs has been revolutionized by the advent of molecular biology and sophisticated computer technology. Approaches now focus on molecular modeling of virtual molecules in an attempt to predict appropriate drug candidates, the use of combinatorial chemistry to generate a large number of potential compounds, and high throughput screening techniques to identify which of the large number of compounds display affinity for the target molecule. Currently, the time line for the development of a new drug is 12 to 15 years. Statistics show that, for each new drug that actually goes to market, approximately 5,000 compounds are initially screened, approximately 5 are eventually deemed suitable for human clinical trials, and only one of the five will gain FDA approval. The entire process can cost as much as $500 million, and the cost of candidates which fail late in the development process incur huge, unrecoverable expenses. Therefore, methodologies which enhance the ability of investigators to predict which compounds are likely to possess specific desired characteristics and elicit the desired effects in target molecules are much sought after in the industry. It is especially desirable if the methodologies can be applied early in the developmental process and thus avoid fruitless developmental endeavors.

Many drug candidates are small molecules which bind to proteins and regulate their function. Frequently, the proteins, especially enzymes, possess allosteric regulatory sites located relatively distant from their active site. The initial interaction of a ligand (e.g. an inhibitor, hormone, substrate, agonist, etc.) may occur at the local, regulatory binding site and typically involves only a few residues. However, the effects of binding are often propagated to the remote active site in the protein and may ultimately involve many residues. Ligand binding to the regulatory site may ultimately activate or inhibit the protein by affecting the ability of the distal site to be binding competent towards an interacting partner in, for example, a signaling cascade. Binding of the ligand to the regulatory site may stabilize or destabilize the distal binding site, therefore affecting an entire molecular or cellular pathway. The chain of events initiated by initial ligand binding thus provides the basis for fundamental biological phenomena such as allosteric regulation, signal transduction and structural stability modification. Whatever the functional expression of the interaction, a necessary condition for proper functioning of the regulatory switch is the coupling (i.e. the atomic "wiring") between the regulatory and active sites.

While much progress has been made with respect to the characterization of ligand binding events, it is still not possible to predict with certainty the outcome of binding at the molecular level. Standard methods of analysis include protein computational analysis, such as molecular mechanics or molecular dynamics. These methods are typically designed to identify a single conformation of a molecule (or molecule-ligand complex) that is predicted to be the most energetically favorable and therefore the most likely to represent the true conformation of the molecule or complex. The methods are generally based on the analysis of only one molecule or complex at a time in the calculations. By performing bond rotations over different dihedral angles, these methods generate a large number of conformations, usually in a sequential manner. The energy of each conformation is computed by using different search or minimization algorithms, and the conformation with the lowest energy is identified.

However, during the past decade, it has become evident that this approach to the study of molecular conformation is inadequate. This is because, in reality, a protein (or other molecule) actually exists in the native state as an ensemble of many thermodynamically available conformational states of varying degrees of population, rather than as a single discrete state. This is in part because the energy of stabilization of the structure of a protein is not evenly distributed throughout the molecule. Proteins are instead characterized by the occurrence of multiple independent local folding/unfolding events, i.e. proteins lack global cooperativity. The degree of population of any given conformational state of the many which are possible is governed by statistical thermodynamics: those states that are the most thermodynamically (energetically) favorable are the most populated. The probability that a protein (or a part of a protein) occupies a given conformation is determined by the Gibbs energy difference between conformations, i.e. the frequency with which a given molecule will "visit" a given conformation is dictated by how energetically favorable the conformation is. More energetically favorable conformations are visited more frequently. The entire system exists in a state of dynamic equilibrium with individual molecules depopulating and repopulating all available conformations. At any one time, the statistical distribution of all molecules within the mix will also accord with the Gibbs energy difference between conformations, in that the more energetically favorable a conformation states will be more highly populated.

This realization, while gratifying, has also complicated the thermodynamic analysis of protein-ligand binding events. Conventional methodology which does not take into account the statistical distribution of molecular conformations is clearly inadequate. It would be highly advantageous to have available methods for the predictive analysis of ligand binding which is based on the thermodynamic assessment of the multiple conformational states of a molecule. Such methods would facilitate the design and selection of promising drug candidates at an early stage of the drug development process.

SUMMARY OF THE INVENTION

It is an object of this invention to provide a computer assisted computational method for creating and displaying a model of a molecule in which, in the model, the residues of the molecule that are affected by the binding of a ligand of interest to the molecule are highlighted. Highlighting of the affected residues permits the visualization of the path of propagation of the binding signal throughout the structure of the molecule.

The method involves the input of the three-dimensional coordinates of the molecule into the programmed computer, generating an ensemble of about 20,000 to 200,000 (or more) partially folded conformational states of the molecule, and determining the Gibbs energy (ΔG) of each conformational state. The binding competent conformational states are then identified and the ΔG values for those states are modified using the equation $$\Delta Gi = \Delta Gi^0 - RT \ln \frac{(1 + Ka, i[X])}{(1 + Ka_{,0}[X])}$$

where $\Delta Gi^0$ is the Gibbs energy in the absence of the ligand X, (i.e. the Gibbs energy of the state as calculated in Equation 2); $Ka_{,0}$ is the binding constant of the ligand to a reference (in this case, the native or template conformation); and Ka,i is the binding constant of the ligand to a given binding competent state i.

The probability of each state in the absence and in the presence of ligand is then calculated from the Gibbs energy data, and a residue level stability constant (κ) in the absence and in the presence of ligand is calculated for each residue of the molecule. κ values in the absence and in the presence of ligand are compared. Those residues in which κ is different in the presence vs the absence of ligand are those which are affected by the binding of ligand. A single representation of the molecule in which those affected residues are highlighted is generated and displayed. By visually observing the highlighted residues on the displayed molecule, it is possible to trace a path of propagation of the ligand-binding induced signal through the body of the molecule. Because κ values are numerical quantities, it is also possible to quantitate the degree of the effect of ligand binding on the individual residues.

BRIEF DESCRIPTION OF THE DRAWINGS

FIG. 1. Flow Chart FIG. 1 depicts the steps of the method. ΔG=Gibbs energy; ΔG*=modified Gibbs energy; P=probability; P*=probability from modified Gibbs energy; bc=binding competent; non-bc=non-binding competent; κ=stability constant; n=number of residues in molecule of interest.

DETAILED DESCRIPTION OF THE PREFERRED EMBODIMENTS OF THE INVENTION

The present invention provides a computer-assisted method for creating and displaying a model of a molecule in which residues that are affected by the binding of a ligand to the molecule are highlighted. By observing the highlighted residues, it is possible to trace the path of propagation of a binding signal through the molecule. For example, it is possible to trace the path of propagation of a binding signal from a regulatory binding site to a distal portion of a molecule. The method may thus be used, for example, to predict the identity of residues of a molecule that are affected by the binding of a ligand to the molecule, to predict the effects of a change in a molecule (e.g. an alteration in a residue) on ligand-binding signal propagation, and so on.

The residues of a molecule that are highlighted are those that are "affected" by a ligand binding to the molecule. The parameter that is measured as an indicator of whether a residue has been affected is the stability of the residue, as defined by an individual residue-level stability constant, κ. The value of κ for any residue is calculated as the ratio of the summed probabilities that the residue is in a native, folded conformation and the summed probabilities that the residue is not in a native conformation, i.e. that it is unfolded (discussed in detail below). In the practice of the present invention, the value of the stability constant for each residue of a molecule is calculated in the presence and absence of a potential ligand. Those residues which exhibit a change in stability constant as a result of the presence of a ligand are those which are affected. By highlighting those residues on the three dimensional structure of the molecule, it is possible to observe the connectivity of the affected residues in space. The connectivity defines the path of propagation of a binding signal through the molecule. Because κ is a discrete value, it is also possible to quantitate the effects of ligand binding on the affected residues using the methods of the instant invention.

The calculation of the stability constant is a multistep process which is based on the ergodic hypothesis of statistical mechanics. This hypothesis states that, for a system in dynamic equilibrium (such as a native state protein which exists in a variety of differentially populated states) the ensemble average of any given property (such as a particular folded conformation) is equivalent to its time average. Unlike conventional methods for the analysis of the energy states of a molecule, in which multiple conformations of the molecule are generated, in applying the ergodic hypothesis multiple copies (states) of the molecule each one having a different single conformation (and associated energy level) are generated. Together, all these copies or states make up a conformational ensemble for the molecule from which different properties may be computed.

The ensemble is generated in a manner similar to that previously described (Hilser & Freire, 1996) except that the method of Hilser & Freire involved an exhaustive enumeration which is computationally unreasonable to implement for proteins containing more than about 150 residues. The modification of that method as described herein is applicable to molecules of any size. To begin, a high resolution structure is obtained for use as a template or native state molecule. This structure may be, for example, from x-ray crystallographic data, from high resolution NMR data, or from a theoretical structure generated by computer modeling. Each element or state in the ensemble is generated by applying a random sampling algorithm (Hilser & Freire, 1996, described below) in order to select a group of residues in the template and switch the conformation of the residues in the selected group to the unfolded conformation. The unfolded state is defined in terms of a set of thermodynamic criteria as detailed in Luque et al. (1996). The selected residues may be contiguous or non-contiguous in sequence.

The unfolded conformation is chosen because it provides a convenient reference state for energy calculations. However, in principle, any other defined reference state may also be used, for example a different conformation of the protein. Each resulting state is characterized by having all residues except the selected ones in the template conformation.

The random sampling algorithm proceeds in two steps. First, the number of residues and the number of sequence segments (windows) in which the selected residues will be placed are randomly selected. Then, the initial locations for all windows are randomly selected. The algorithm checks that the windows do not overlap. A minimum window size can be specified prior to the calculations. The window size will typically be in the range of 4–12. In a preferred embodiment of the present invention, the window size is 8. The procedure is repeated until a satisfactory statistical sample is obtained. In the method described by Hilser & Freire, an exhaustive computational analysis was performed. However, for proteins in excess of 150 residues, such computations would be intractable. For example, a protein of 500 residues with a window of size 8 will generate on the order of $10^{28}$ states if the calculation is performed exhaustively. Therefore, the procedure has been modified for larger proteins (e.g. those with over about 150 residues). In the case of a larger protein, a sufficient number of states are generated to achieve convergence to a stable ensemble average. In general, an ensemble of states numbering from about 20,000 to about 200,000 with a degree of unfolding not exceeding 0.5 are generated. are sufficient. In a preferred embodiment of the present invention, a minimum of 20,000 randomly generated states will be generated. This number of states, though not exhaustive, is sufficient to achieve convergence to a stable ensemble average. This is likely because, under native conditions, states with extensive unfolding have a negligible probability of existing. However, those of skill in the art will recognize that more states may be generated, depending on factors such as the size of the molecule under analysis, and the desired degree of accuracy.

This procedure creates an ensemble containing a collection of elements (protein conformational states) in which each state is represented by a single copy. In order to calculate κ values for each residue of the subject molecule from the collection of states, it is necessary to calculate the probability of each state. This is accomplished by applying an art-recognized equation for the Gibbs energy function to each member in the ensemble because, according to standard statistical thermodynamic theory, the probability, $P_1$, of any state in an ensemble is given by the following equation:

$$Pi = \frac{e^{\frac{-\Delta G_i}{RT}}}{\sum_j e^{\frac{-\Delta G_j}{RT}}} \quad (1)$$

where $\Delta G_1$ is the Gibbs energy of state i, and the denominator is the sum of the statistical weights of all states in the ensemble, R is the gas constant and T is the absolute temperature (°K). The sum in the denominator runs over all the states in the ensemble.

Those of skill in the art will recognize that the exact form of the Gibbs energy function and the values of the accompanying coefficients are under continuous refinement and therefore may vary, depending on the source. All such variations of the Gibbs energy function may be utilized to carry out the methods of the present invention. In a preferred embodiment of the present invention, the following structurally parameterized Gibbs energy function is utilized:

$$\Delta G = E_{hard} + \sum_{\substack{atom \\ pairs}} [a_i + b_i \left(\frac{R_{min}}{R_w}\right)^6]_i \Delta ASA_i \rightarrow \Delta H_{intrinsic} \quad (2)$$

$$- T \sum_i a_{c,i}(\Delta ASA_i) \ln\left[\frac{T}{T_i^*}\right] \rightarrow \Delta S_{solvation}$$

$$- T\Delta S_{conf} \rightarrow \Delta S_{conformation}$$

$$- T\Delta S_{te} \rightarrow \Delta S_{translation}$$

$$+ 332 \left[\sum_i \frac{Z_i^2}{2r_i}\left[\frac{1}{D} - \frac{1}{D_{ref}}\right] + Z_i \sum_j \frac{Z_j}{Dr_{i,j}}\right] \rightarrow \Delta G_{electrostatic}$$

$$+ \Delta G_{proton}(pK, pH) \rightarrow \Delta G_{protonation}$$

where the different enthalpic and entropic terms are obtained from the structural parameterization of the folding and binding energetics described by Luque and Freire (1998). The probability of each state may then calculated from equation (1).

Up to now in the procedure, approximately 20,000–200,000 (or more) values are associated with the subject molecule. In order to generate a useful display of the information contained in those values, the multiple values are "mapped" into a single representation of the molecule. Mapping is carried out by performing a mathematical transformation of the probabilities of the states in the ensemble to residue-level probabilities. In general, an ensemble property φ (such as the property that a residue exists in a particular conformation) can be mapped to a single molecule because the probability that a particular residue y exhibits a property is equal to the sum of the probabilities of all members of the ensemble that exhibit that property:

$$P_{r,y,\phi} = \sum_i P_{i,y,\phi} \quad (3)$$

$$y \rightarrow \phi$$

where the summation runs over all the states in which residue y exhibits property φ. $P_{r,y,\phi}$ is calculated for each residue in the protein. For example, in the case of a residue exhibiting a particular conformation, the probability that the residue exhibits the particular conformation is equal to the summation of the probabilities of all states in the ensemble in which the residue exhibits that particular conformation.

Residue-level probabilities can also be defined as the joint probabilities that a group or subset of residues will show some specific property. For example, the probability that the residues forming a binding site are in the proper conformation and therefore that the site is binding competent, can be defined. In this case, $P_{r,\{y\},\phi}$ is defined as the joint probability that the subset of residues {y} that define a binding site, φ, are in the proper conformation. $P_{r,\{y\},\phi}$ is equal to the sum of the probabilities of all the states in which the subset of residues that form the binding site, {y}, are in the proper conformation:

$$P_{r,\{y\},\phi} = \sum_i P_{i,\{y\},\phi} \quad (4)$$

$$\{y\} \rightarrow \phi$$

where the summation runs over all the states in which the residues that define the binding site are in the proper conformation. Joint probabilities can be defined for any other arbitrary property for which the participation of more than one residue is required.

In an adaptation of this mathematical relationship, Hilser & Freire (1996) defined the stability constant, κ, for each residue of a protein. The stability constant is the ratio of the sum of the probabilities of all the states in an ensemble in which a residue y is in the native state, and the sum of the probabilities of all states in the ensemble in which it is not:

$$\kappa_y = \frac{\sum_i P_{i,y=native}}{\sum_i P_{i,y \neq native}} \quad (5)$$

In the present invention, the calculation of the residue stability constant is the mathematical transformation that converts the probabilities of the states in the ensemble to residue-level probabilities, thus allowing the mapping of a state level attribute (probability) to the level of the individual residues. However, in the practice of the present invention, the definition of the stability constant is extended to include the effects of ligand binding to a protein.

This is accomplished by modifying the calculation of the Gibbs energy for the conformational states of a molecule to which a ligand binds in order to account for the effects of ligand binding on the energy level (and thus the probability) of those states. Since κ is a ratio of probabilities (calculated from the modified Gibbs energies) the modification is ultimately reflected in the value of κ at the residue level.

To account for the effects of ligand binding, the Gibbs energies of the conformational states of a molecule in which the binding site is formed (i.e. those states which are binding competent) in an ensemble representing a molecule for which X is a ligand are modified according to the equation:

$$\Delta Gi = \Delta Gi^0 - RT\ln\frac{(1+Ka,i[X])}{(1+Ka,0[X])} \quad (6)$$

where $\Delta Gi^0$ is the Gibbs energy in the absence of the ligand X, (i.e. the Gibbs energy of the state as calculated in Equation 2); $Ka,0$ is the binding constant of the ligand to a reference (in this case, the native or template conformation); and $Ka,i$ is the binding constant of the ligand to a given binding competent state i. The Gibbs energy of each binding competent conformational state in an ensemble will be affected in a manner dependent on the magnitude of the binding constants of the ligand for that state. Accordingly, those states that are able to bind the ligand will be energetically stabilized with respect to those states that are not able to bind the ligand, causing a change in the probability distribution of all states.

In the practice of the present invention, equation 6 is used to modify the Gibbs energy of those states which are binding competent, i.e. those sites in which the binding site for ligand X is formed. This necessitates the identification of the residues involved in binding (the binding site determinants) and the selection of those states in the ensemble in which those residues are in a binding competent conformation. Further, both $Ka,0$ and $Ka,i$ must be determined, either computationally or by experimental means. Identification of the binding site determinants is accomplished by utilizing high resolution structures of the free protein, the free ligand, and the protein-ligand complex. The contribution of each individual residue to the Gibbs energy of binding is calculated by applying a parameterized Gibbs energy function (e.g. equation 4) to the high resolution structures. Each thermodynamic quantity, $\Delta Y$, that contributes to the Gibbs energy (where $\Delta Y$ refers to $\Delta ASA$, $\Delta H$, $\Delta S$, $\Delta G$, etc. as listed in equation 4) is evaluated at the residue level as:

$$\Delta Y = Y_{complex} - Y_{free\ protein} - Y_{free\ ligand} \quad (7)$$

The calculation of the Gibbs energy of binding permits prediction of 1) the binding affinity of the ligand and 2) the contribution of each residue to the binding affinity. Those residues that contribute the most to the Gibbs energy of binding define the binding determinants of the binding site, i.e. those residues that contribute more than about 100 cal/mol to the Gibbs energy of binding.

Identification of the binding determinants in this manner allows the identification of those states which are binding competent: protein conformational states of the ensemble are considered to be binding competent if the residues that constitute the binding determinants are in the native (template or folded) conformation in those states. The Gibbs energy of each binding competent state is modified by equation 6 by setting [X] equal to a given concentration of ligand. While any concentration can be used in the calculation, in a preferred embodiment the concentration is the one that elicits 99% saturation. This concentration is given by $[X]=100/K_{1,0}$. Note that, if no ligand is present, then [X]=0 and Equation 6 becomes equivalent to Equation 4.

The modified Gibbs energy calculations for the binding competent states can be combined with the Gibbs energy calculations for the non-binding competent states to generate two complete sets of 20,000 (minimum) Gibbs energy values. One set represents the Gibbs energies of all states (binding competent and non-binding competent) in the presence of ligand. For this set, the Gibbs energy values (Equation 2) of binding competent states have been modified by Equation 6 with [X]=a defined concentration of ligand. The other set represents the Gibbs energies of all states in the absence of ligand. For this latter state, the Gibbs energy values of binding competent states have been calculated with Equation 2 (or alternatively, modified by Equation 6 with [X]=0). All Gibbs energy values for non-binding competent states are calculated from Equation 2.

State probabilities are calculated from the Gibbs energy values of both sets separately using equation 1.

The goal of the computational method of the instant invention is to calculate individual residue level stability constants (equation 5). Equation 5 utilizes 1) the summation of the probabilities of all states in an ensemble that are in the native conformation (i.e. are binding competent and 2) the summation of the probabilities of all states in an ensemble that are not binding competent. Two sets of κ values are calculated in this manner for all residues in the protein, one from each of the sets of probability data. This gives two sets of residue level stability constants for each residue: one set represents κ values in the presence of a defined concentration of ligand, and the other represents κ values in the absence of ligand. The stability constants obtained for each residue in the two different sets are compared. Those residues that exhibit a difference in stability constant in the presence vs the absence of ligand are those that are affected by ligand binding. The difference is expressed as a free energy function $\Delta\Delta G = -RT \ln \kappa_{[x]} + RT \ln \kappa_{[0]}$.

The affected residues so identified can be highlighted in a single three dimensional display of the molecule. The highlighted residues will trace a path through the body of the molecule from the ligand binding site to distal portions of the molecule. This path represents the path of propagation of the ligand-induced signal. In addition, because κ values are discrete numbers, the effect of ligand binding on individual residues may be quantified.

Figure 1:
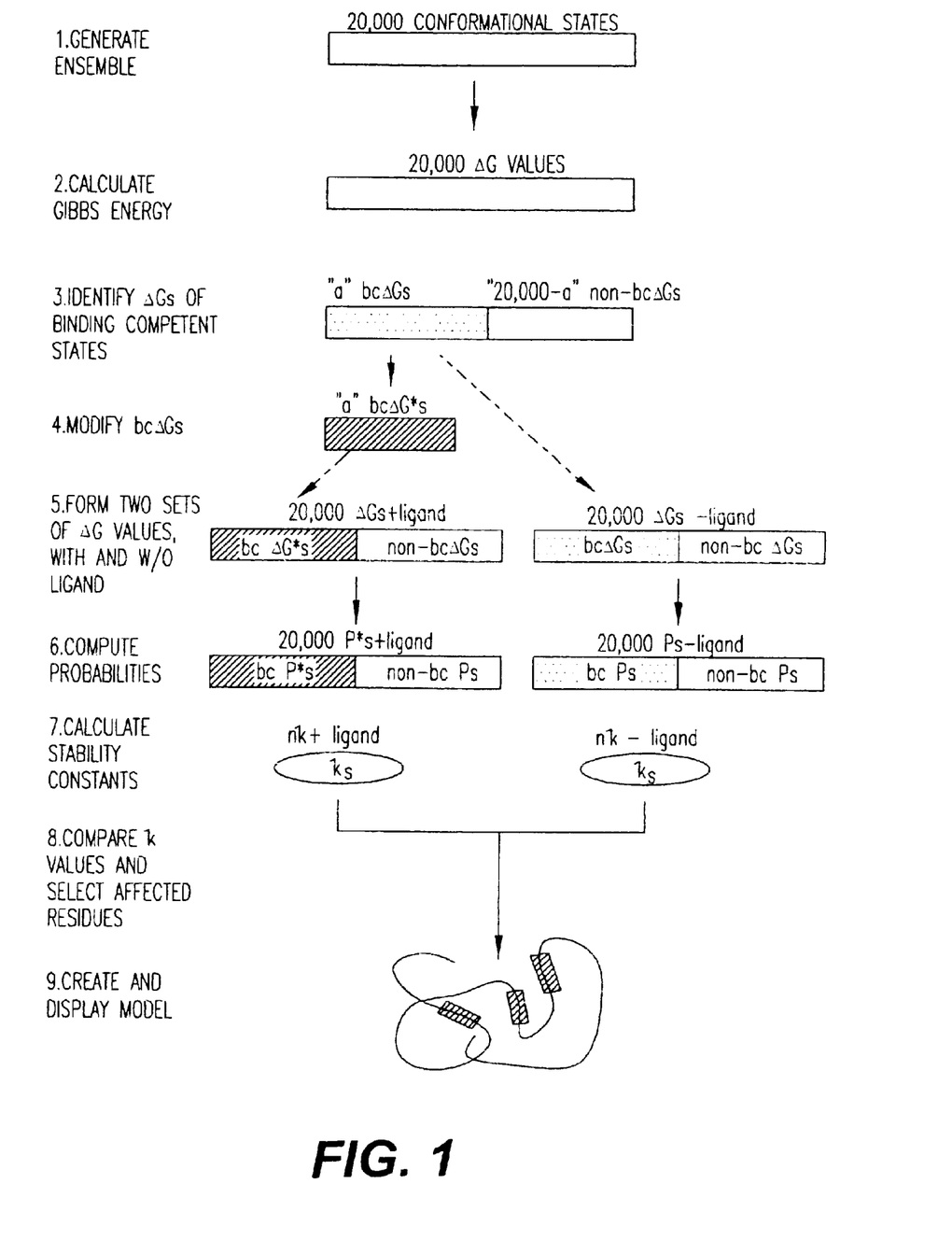

The steps of the instant invention are schematically outlined in the flow chart provided in FIG. 1. In Step 1, an ensemble of conformational states (in this case, 20,000) is generated. In Step 2, ΔG is calculated for all states. In Step 3, those states that are binding competent are identified. That permits the division of the ΔG values for all states of the ensemble into two groups: those which are binding competent ("bc", the number of theses values is "a") and those which are non-binding competent ("non-bc", the number of non-bc values is 20,000−a). In Step 4, the ΔG values for all binding competent states are modified (Equation 6) to yield ΔG* values. In Step 5, two sets of ΔG values for all states are formed, one "in the presence of ligand" and the other "in the absence of ligand". In the former, the ΔG values that are used for the bc states are the modified ΔG* values; in the latter, non-modified ΔG values are used for the bc states. In both sets, non-modified ΔG values are used for the non-bc states. In Step 6, the probabilities of all states are calculated. In Step 7, the stability constants for each residue are calculated. In Step 8, the stability constants in the presence of ligand and in the absence of ligand are compared. In Step 9, the affected residues (those which exhibit a difference in stability constant in the presence vs in the absence of ligand) are identified. In Step 10, the affected residues are displayed and highlighted in a 3-D representation of the molecule.

In a preferred embodiment of the instant invention, the molecule that is analyzed by the computational method of the instant invention is a protein. However, those of skill in the art will recognize that other molecules may also be analyzed in this manner. The molecules for which this method may be used include any molecule which binds a ligand. Such molecules include but are not limited to proteins, nucleotides such as DNA and RNA, saccharides, lipids, synthetic polymers or other synthetic molecular structures e.g. macromolecular rings, "cages", chelating molecules, etc. Any molecule that is amenable to the method of analysis described herein may be the subject of the method of the instant invention. Further, the molecules may be either naturally occurring or synthetic.

By "ligand" we mean any molecule that binds to a molecule as described above. The ligand may be of the same molecular type as the molecule (e.g. both "molecule" and "ligand" may be a protein or a fragment of a protein) or they may be different (e.g. the "molecule" may be a protein and the "ligand" may be a small, non-proteinaceous molecule such as an antibiotic, a metal, a saccharide, a lipid, a nucleotide or a nucleotide polymer, and the like.) The "ligand" may have a lesser, greater, or the same molecular weight as the "molecule". In a preferred embodiment of the instant invention, the molecule is a protein.

The terms "molecule" and "ligand" are functional in nature in that, at the discretion of the person using the method, either of the two entities involved in binding may be defined as the "molecule" and the other as the "ligand", and the definition can change from one use of the method to another.

By "binding" of a ligand we mean that a portion of the atoms which make up the ligand become located within bonding distance of a portion of the atoms which make up the molecule. By "within bonding distance" we mean<about 5 Å. Such bonding may be covalent or non-covalent in nature.

The method of the present invention is a computer-assisted method. As such, the method utilizes a programmed computer which includes a processor (1 of FIG. 2), an input device such as a keyboard or wand (2 of FIG. 2), and an output device such as a display monitor (3 of FIG. 2). Examples of processors which may be utilized in the practice of the present invention are well-known to those of skill in the art, as are examples of input and output devices which may be utilized in the practice of the present invention.

Figure 2:
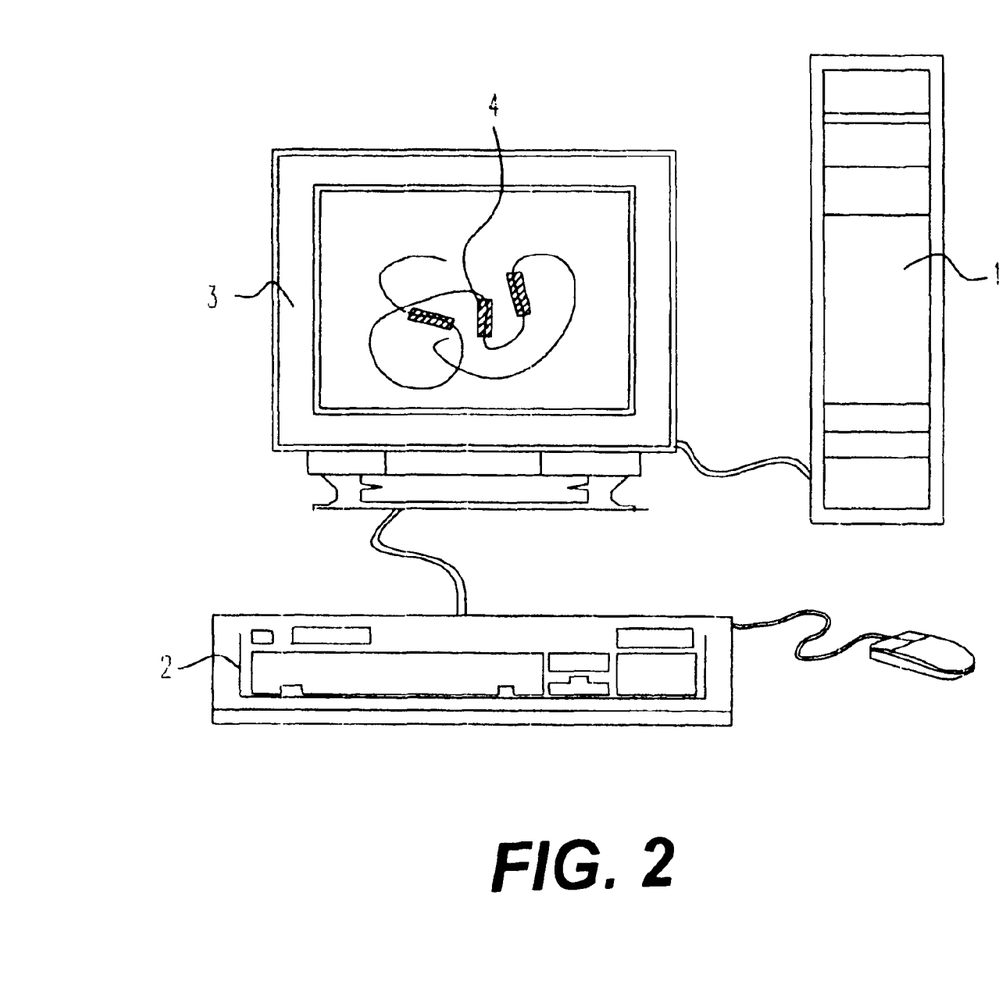
FIG. 2. 1=processor; 2=input device; 3=output device; 4=model of molecule with affected residues highlighted.

In the first step of the method, data including three-dimensional coordinates of the molecule are input using an input device such as a keyboard or wand into the programmed computer. Systems for obtaining and manipulating three-dimensional coordinates of molecules are readily available and well-known to those of skill in the art. The three-dimensional coordinates may be experimentally obtained (e.g. from x-ray crystallographic or high resolution nuclear magnetic resonance data, either directly or from a data bank, for example from the Protein Database), or they may be generated theoretically from, for example, a computer program designed for building and manipulating molecules in three dimensions.

In the practice of the present invention, the affected residues are highlighted in a 3-D representation of the native protein (4 of FIG. 2). The residues may be highlighted by any of many different means known to those of skill in the art. For example, they may be depicted in a color that contrasts with that of the other residues of the protein, or by shading, or by the addition of marks such as stripes or dots, and the like. Further, the protein may be displayed in any of several ways known to those of skill in the art, such as in the form of a "ball and stick" model, a ribbon diagram, surface model, and the like. Any means of displaying the protein and highlighting the affected residues may be utilized in the practice of the present invention, so long as the affected residues can be distinguished in the resulting 3-D image. In a preferred embodiment of the instant invention, the affected residues are color coded.

The following examples are given merely to illustrate the practice of the present invention and should not be construed so as to limit the invention in any way.

EXAMPLES

Example 1

Application to the Allosteric Protein Glycerol Kinase

Glycerol kinase is a protein of 500 amino acids. An allosteric inhibitor of this enzyme is the protein IIAGlc. It would have been impossible to analyze the conformational states of this enzyme with an exhaustive algorithm since on the order of $10^{28}$ would have been generated, a number well beyond the reach of any computational method.

Figure 3A:
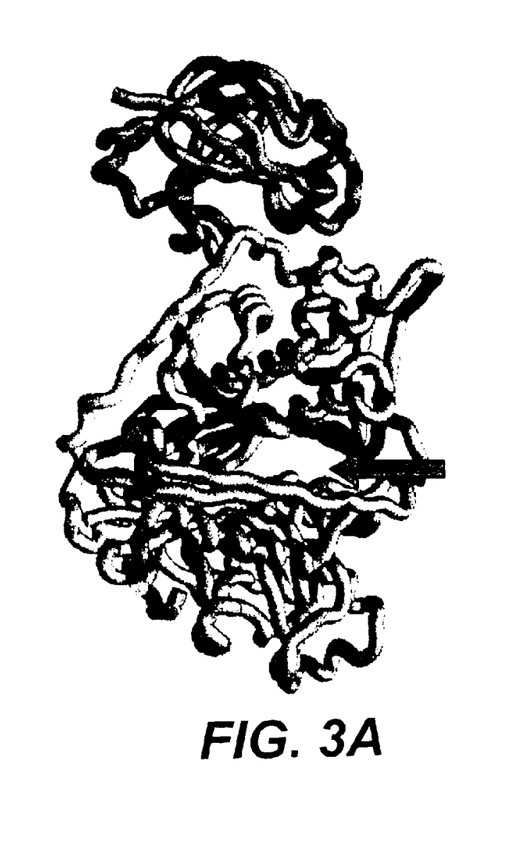
FIGS. 3A–C. Visualization of the path of propagation of ligand binding signal in glycerol kinase. A: the complex between glycerol kinase (white) and the allosteric regulator IIAGlc (black). The arrow indicates the location of the catalytic site. B. The structural distribution of the stability of glycerol kinase (black=stable; white=unstable). The arrow indicates the regulatory binding site. The regulatory binding site for IIAGlc contains regions of low structural stability. In the absence of IIAGlc, these regions do not interact strongly with the rest of the protein. C. The propagation of cooperative interactions triggered by the binding of IIAGlc. Glycerol kinase has been coded according to the magnitude of the effect of IIAGlc binding on the stability constants per residue. The residues that define the binding site are affected the most; however, the effect extends to regions far away from the binding site (black). Of particular importance from the point of view of allosteric regulation appears to be a stretch of residues that connects the regulatory and catalytic domains.
Figure 3B:
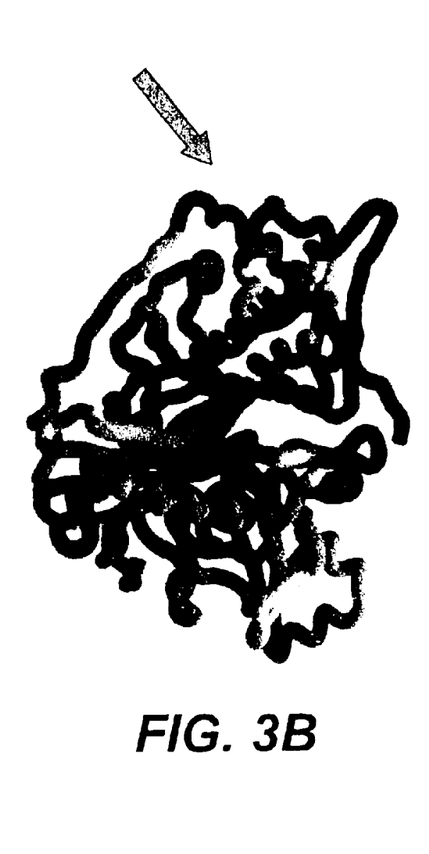

IIAGlc binds to glycerol kinase at a site located more than 30 Å away from the active site. The regulatory binding site is defined by a loop leading to the carboxy terminal helix of glycerol kinase and the first two and one half turns of that helix (residues 471–482). IIAGlc also makes contacts with the loop defined by Leu 426 and Val 430. Finally, Glu 43 in IIAGlc makes a strong salt bridge with Arg 402 in the adjacent loop between Gly 400 and Ala 405. FIG. 3A shows the binding surface between these two proteins. In FIG. 3B, the structure of glycerol kinase has been coded according to the residue stability constants calculated for the unligated form. It is clear that the allosteric binding site is defined to a large extent by some of the least stable regions of glycerol kinase. In the absence of the inhibitor these regions cannot establish the necessary interactions required to drive the catalytic site into its inactive form. The binding of IIAGlc stabilizes this region into a conformation capable of establishing specific contacts with adjacent regions that eventually result in the stabilization of the inactive conformation of the catalytic site. Glycerol kinase provides a clear example of the general requirement that the site of origin for the transmission of signals to distal sites within protein structures cannot be binding competent towards the signaling ligand in the unligated form. In its free form the site must either occupy a different conformation or exhibit low stability as in the case of glycerol kinase.

Figure 3C:
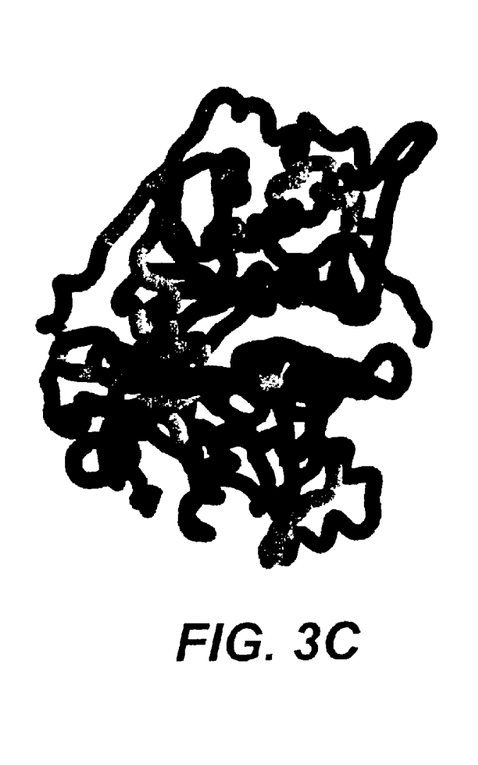

Additional calculations permit an evaluation of the structural propagation of the cooperative effects triggered by the binding of IIAGlc on glycerol kinase (FIG. 3C). As seen in the figure, the area in immediate contact with IIAGlc (the binding site) is structurally stabilized by the binding of the inhibitor (black). The magnitude of the stabilization provided by IIAGlc depends on the concentration of inhibitor and is equal to $-RT\ln(1+Ka[IIAGlc])$. The association constant of IIAGlc to glycerol kinase is close to $10^5$ $M^{-1}$ at 25° C. The additional Gibbs energy of stabilization provided by the binding of IIAGlc is not circumscribed to the binding site region. It is transmitted through cooperative interactions to regions away from the binding site. These cooperative interactions do not involve all residues in glycerol kinase, but only a relatively small subset. As seen in the figure, the algorithm predicts that the major effect of IIAGlc involves a narrow stretch of amino acids connecting the allosteric site with the catalytic site. These amino acids run on the opposite side to the opening of the catalytic site (see figure) and define a cooperative hinge mechanism that switches the catalytic site between active and inactive conformations. This stretch of amino acids connects the regulatory and active sites and correlates their behavior.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

References

Freire E. (1997). The statistical thermodynamic linkage between conformational and binding equilibrium. *Adv. Prot. Chem.* 51, 255–279.

Freire, E. (1999). The Propagation of Binding Interactions to Remote Sites in Proteins. Analysis of the Binding of the Monoclonal Antibody Dl.3 to Lysozyme, *Proc. Natl. Acad. Sci.* (*USA*) 96, 10118–10122.

Hilser, V. J. & Freire, E. (1996). Structure based calculation of the equilibrium folding pathway of proteins. Correlation with hydrogen exchange protection factors. *J. Mol. Biol.* 262, 756–772.

Luque, I, Mayonga, O. L. and Freire, E. (1996) Structure-based thermodynamic scale of alpha-helix propensities in amino acids. *Biochemistry* 35, 13681–13688.

Luque, I. & Freire, E. (1998). A system for the structure-based prediction of binding affinities and molecular design of peptide ligands. *Methods. Enzymol.* 295, 100–127.

What is claimed is:

1. A computer-assisted method for creating and displaying a model of a molecule in which the residues of said molecule that are affected by binding of a ligand to said molecule are highlighted using a programmed computer including a processor, an input device, and an output device, comprising, inputting into said programmed computer, through the input device, data including an identity and three-dimensional coordinates of said molecule, generating, using the processor, a conformational ensemble for said molecule, wherein said conformational ensemble is comprised of a number of conformational states of said molecule sufficient to achieve convergence to a stable ensemble average, determining, using the processor, a predicted Gibbs energy for each of said conformational states, identifying, using the processor, binding competent conformational states, wherein said step of identifying binding competent conformational states comprises the steps of i) ascertaining a contribution of each residue of said conformational states in said ensemble to the Gibbs energy of binding for said ligand; ii) defining binding determinant residues, wherein said binding determinant residues contribute in excess of about 100 cal/mole to the Gibbs energy of binding, and iii) establishing as binding competent conformational states those conformational states in which said binding determinant residues are in a native conformation, modifying said predicted Gibbs energy for said binding competent conformational states to form a modified Gibbs energy using an equation $$\Delta Gi = \Delta Gi^0 - RT\ln\frac{(1 + Ka, i[X])}{(1 + Ka,_0 [X])}$$

wherein $\Delta Gi$ is said modified Gibbs energy, $\Delta Gi^0$ is said predicted Gibbs energy, R is a gas constant, T is an absolute temperature, $Ka,_0$ is a binding constant to a reference state, $Ka,_i$ is a binding constant to a given binding competent conformational state, and [X] is a concentration of said ligand, forming, using said processor, a first and second set of Gibbs energy values, wherein said first set of Gibbs energy values represents Gibbs energy values in the presence of said ligand and said second set of Gibbs energy values represents Gibbs energy values in the absence of said ligand, computing, using the processor, a first set of probabilities from said first set of Gibbs energy values and a second set second of probabilities from said second set of Gibbs energy values, wherein said first set of probabilities represents probability values in the presence of said ligand and said second set of probabilities represents probability values in the absence of said ligand, calculating, using the processor, a first set of residue stability constants in the presence of ligand from said first set of probabilities and a second set of residue stability constants in the absence of ligand from said second set of probabilities, comparing, using the processor, said first and second sets of residue stability constants, selecting affected residues of said molecule, wherein said affected residues exhibit a difference in stability constant in said first and said second set of stability constants, creating, using the processor, a model of said molecule wherein said affected residues are highlighted, and displaying, using the output device, said model of said molecule wherein said affected residues are highlighted.

2. The method of claim 1 wherein said molecule is a protein.

3. A computer program product comprising a computer-readable medium having stored thereon a computer program including instructions for causing a computer to:

receive data including an identity and three-dimensional coordinates of a molecule, generate a conformational ensemble for said molecule, wherein said conformational ensemble is comprised of a plurality of conformational states of said molecule, determine a predicted Gibbs energy for each of said plurality of states in said conformational ensemble, identify binding competent conformational states, wherein said instruction to identify binding competent conformational states comprises instructions to i) ascertain a contribution of each residue of said conformational states in said ensemble to the Gibbs energy of binding for said ligand: ii) define binding determinant residues, wherein said binding determinant residues contribute in excess of about 100 cal/mole to the Gibbs energy of binding, and iii) establish as binding competent conformational states those conformational states in which said binding determinant residues are in a native conformation, modify said predicted Gibbs energy for said binding competent conformational states to form a modified Gibbs energy using an equation $$\Delta Gi = \Delta Gi^0 - RT\ln\frac{(1 + Ka,i[X])}{(1 + Ka,_0 [X])}$$

wherein $\Delta Gi$ is said modified Gibbs energy, $\Delta Gi^0$ is said predicted Gibbs energy, R is a gas constant, T is an absolute temperature, $Ka,_0$ is a binding constant to a reference state, $Ka,_i$ is a binding constant to a given binding competent conformational state, and [X] is a concentration of said ligand, compute a first set of probabilities from said first set of Gibbs energy values and a second set second of probabilities from said second set of Gibbs energy values, wherein said first set of probabilities represents probability values in the presence of said ligand and said second set of probabilities represents probability values in the absence of said ligand, calculate a first set of residue stability constants in the presence of ligand from said first set of probabilities and a second set of residue stability constants in the absence of ligand from said second set of probabilities, compare said first and second sets of residue stability constants, select affected residues of said molecule, wherein said affected residues exhibit a difference in stability constant in said first and said second set of stability constants, create a model of said molecule wherein said affected residues are highlighted, and display said model of said molecule.

4. The computer program product of claim 3 wherein said molecule is a protein.

* * * * *